United States Patent [19]
Heikkilä-Hoikka et al.

[11] Patent Number: 5,866,556
[45] Date of Patent: Feb. 2, 1999

[54] PYRIDINYLBISPHOSPHONATES FOR USE AS A THERAPEUTICAL AGENT

[75] Inventors: Marjaana Heikkilä-Hoikka, Vanhalinna; Hannu Nikander, Paattinen; Ritva Hannuniemi, Kuusisto; Leena Laurén, Turku; Terttu Kleimola, Littoinen; Sirpa Liukko-Sipi, Vinkkilä; Kalervo Väänänen, Oulu; Raija Sellman, Turku, all of Finland

[73] Assignee: Leiras Oy, Turku, Finland

[21] Appl. No.: 750,355

[22] PCT Filed: Jun. 2, 1995

[86] PCT No.: PCT/FI95/00315

§ 371 Date: Dec. 6, 1996

§ 102(e) Date: Dec. 6, 1996

[87] PCT Pub. No.: WO95/33466

PCT Pub. Date: Dec. 14, 1995

[30] Foreign Application Priority Data

Jun. 9, 1994 [SE] Sweden .................... 9402001

[51] Int. Cl.$^6$ .................... C07F 9/58; A61K 31/675
[52] U.S. Cl. .................... 514/89; 546/22; 546/24
[58] Field of Search .................... 546/22, 24; 514/89

[56] References Cited

U.S. PATENT DOCUMENTS

| 4,447,256 | 5/1984 | Suzuki et al. | 504/195 |
| 4,973,576 | 11/1990 | Sakamoto et al. | 514/92 |

FOREIGN PATENT DOCUMENTS

| 0 186 405 A2 | 2/1986 | European Pat. Off. |
| 0 282 309 A2 | 9/1988 | European Pat. Off. |

OTHER PUBLICATIONS

Chemical Abstracts, Vol. 101(21),abst.192,195r,Nov. 19,1984.
Chemical Abstracts, vol.105,(26),abst.No.232,453q,Dec. 29,1986.
Chemical Abstracts, vol.106(12),abst.No.90180t,Mar. 23, 1987.
Chemical Abstracts, vol.109(25),abst.No.222,488y,Dec. 19, 1988.
Chemical Abstracts,Vol.117(25),abst.No.251,556–q,Dec. 21, 1992.

*Primary Examiner*—Alan L. Rotman

[57] ABSTRACT

The present invention relates to certain optionally ring substituted pyridinylaminomethylidene bisphosphonic acid tetralkyl esters (I) and their use for the treatment of bone diseases, such as osteolytic bone diseases due to malignancy, Paget's disease and primary and secondary osteoporosis.

6 Claims, No Drawings

PYRIDINYLBISPHOSPHONATES FOR USE AS A THERAPEUTICAL AGENT

CROSS-REFERENCE

This application is a 371 of PCT/FI 95/00315 filed Jun. 2, 1995.

The present invention relates to a specific group of pyridylbisphosphonic acid tetraesters for use as a therapeutical agent, in particular for use in bone diseases.

Bisphosphonates are therapeutic agents for the treatment of pathological bone destruction of various origins, such as osteolytic bone diseases due to malignancy, Paget's disease, and osteoporosis. They are analogues of the physiologically occurring inorganic pyrophosphates. The basic P-C-P structure of the bisphosphonates makes it possible to form a great number of different compounds either by changing the side chains of the carbon atom or by an addition onto the phosphates.

In general, bisphosphonates inhibit osteoclasts, cells, which are responsible for the bone resorption. Known bisphosphonates bound to the bone matrix enter resorbing osteoclasts and reduce the activity of osteoclasts. They inhibit bone resorption both in vitro and in vivo. Limited absorption from the gastrointestinal tract, fast disappearance in bone tissue, and unchanged excretion in urine are all characteristics of known bisphosphonates.

The present innovation is based on the idea of providing bisphosphonate derivatives with high oral bioavailability and with low affinity to bone. This is to avoid side-effect without loosing the antiresorptive activity.

In the patents U.S. Pat. No. 4,447,256, DE 28 31 578 (Suzuld et al.); JP 55089210, JP 55098105, JP 55043054, JP 55043055 (Nissan Chemical industries) a process is disclosed for the preparation of some pyridinylaminomethyl-enebisphosphonic acid tetraalkylesters. According to the patents the compounds may be used as herbicides.

In the patent EP 337 706 (Isomura et al.) the preparation of cyclyl- or heterocyclyl substituted aminomethylenebisphosphonic acid tetraesters is disclosed, wherein the ring substituent is either partly or fully saturated. The tetraesters were not tested.

In the patent U.S. Pat. No. 4,973,576 (Sakamoto et al.) some isox- azolyl substituted aminomethylenebisphosphonic acid tetraalkylesters are disclosed, but they have basicly been tested in arthritis. Their oral bioavailability is low.

In the patent EP 282 309 azole-aminomethylenebisphosphonic acids and lower alkyl esters are disclosed. The tetraesters were not tested.

In the patent EP 325 482 cycloalkyl-aminomethylenebisphosphonic acids and esters are disclosed. The tetraesters were not tested.

The present invention is directed at a group of pyridinyl-bisphosphonates with new pharmacological and pharmacokinetic profiles. These new pyridinylbisphosphonates do not inhibit bone resorption in vitro but they inhibit bone resorption in vivo.

Pyridylbisphosphonates do not bind to bone matrix and they seem to need metabolic activation.

The invention thus concerns pyridyl-aminomethylenebisphosphonic acid tetraalkylesters, which are optionally substituted at the pyridine ring, specifically methylenebisphosphonic acid derivatives of the general formula I

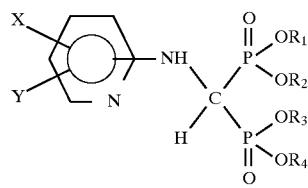

in which formula
each of the groups $R_1$ to $R_4$ is straight or branched saturated $C_1$–$C_5$-alkyl group, each of X and Y is independently hydrogen, straight or branched saturated $C_1$–$C_5$-alkyl group, halogen, hydroxyl, $C_1$–$C_5$-alkoxy, benzyloxy, acyloxy, nitro, trifluoromethyl group or $NR_5R_6$, wherein $R_5$ and $R_6$ are the same or different and are hydrogen, $C_1$–$C_5$-allyl or -acyl, for use as therapeutically active agents.

The groups X and Y, as well as the amino group of the methylenebisphosphonic acid ester frame can substitute any one of the positions 2 to 6 of the pyridyl ring. The groups X and Y are preferably hydrogen or hydroxyl groups, in the latter meaning one or two hydroxyl groups being preferred. The pyridinyl group is preferably a 2-pyridinyl group.

Halogen is fluorine, chlorine, bromine or iodine.

The $C_1$–$C_5$-alkyl group is straight or branched, such as methyl, ethyl, n-, i-propyl, n-, i- and t-butyl, or -pentyl, preferably methyl or ethyl. The allyl group in the alkoxy group as defined for X and Y can have the meaning given above, and is preferably methyl or ethyl.

Acyl in the definition of acyloxy as X and Y, or in the definition of $R_5$ or $R_6$, is preferably a lower allyl carbonyl group, wherein the alkyl group contains from 1–5 C-atoms and has the meaning given above, and is preferably methyl or ethyl. The groups $R_1$ to $R_4$ are preferably the same, and advantageously ethyl.

Preferred compounds of the present invention are the compounds identified as follows:

[(2-pyridinylamino)methylidene]bisphosphonic acid tetraethylester

[[(3-Hydroxy-2-pyridinyl)amino]methylidene]bisphosphonic acid tetraethylester

[[(6-Methoxy-3-pyridinyl)amino]methylidene]bisphosphonic acid tetraethylester

[(4-Pyridinylamino)methylidene]bisphosphonic acid tetraethylester

[[(5-Chloro-2-pyridinyl)amino]methylidene]bisphosphonic acid tetraethylester

[[(5-Methoxy-2-pyridinyl)amino]methylidene]bisphosphonic acid tetraethylester

[[(6-Amino-2-pyridinyl)amino]methylidene]bisphosphonic acid tetraethylester

[[(3-Nitro-2-pyridinyl)amino]methylidene]bisphosphonic acid tetraethylester

[[(3,5-Dichloro-2-pyridinyl)amino]methylidene]bisphosphonic acid tetraethylester

[[(6-Hydroxy-3-pyridinyl)amino]methylidene]bisphosphonic acid tetraethylester

[[(5-Hydroxy-2-pyridinyl)amino]methylidene]bisphosphonic acid tetraethylester

[[(3-Chloro-5-trifluoromethyl-pyridinyl)amino]methylidene]-bisphosphonic acid tetraethylester

[[(2-Chloro-3-pyridinyl)aminio]methylidene]bisphosphonic acid tetraethylester

[[(6-Chloro-3-pyridinyl)amino]methylidene]bisphosphonic acid tetraethylester

[[(3-Benzyloxy-2-pyridinyl)amino]methylidene]bisphosphonic acid tetraethylester

[[(5-Nitro-2-pyridinyl)amino]methylidene]bisphosphonic acid tetraethylester
[[(5-Benzyloxy-2-pyridinyl)amino]methylidene] bisphosphonic acid tetraethylester The N-substituted (aminoalkylidene)bisphosphonic acid tetraesters may be prepared in a known manner e.g. by reacting an amino substituted compound with alkyl orthoformate and reacting the imino ether derivative obtained as an intermediate with diakyl phosphite, either as such or in purified form.

In a second method, a suitable aminopyridine is first reacted with a mixture of formic acid/acetic anhydride. The obtained formamide is then reacted with phosphorus trihalogenide and trialkylphosphite.

Aminoalkylidenebisphosphonic acid tetraesters may also be prepared by letting a aminopyridine derivative react with a halomethylphosphonate and the thus obtained compound, after bromination, is reacted with trialkylphosphite (Schrader et al. Synthesis (1986), 372).

The compounds are useful for the treatment of bone diseases, such as osteolytic bone diseases due to malignancy, Paget's disease and primary and secondary osteoporosis, in a mammal.

The activity of the compounds was verfied by animal and in vitro studies, the methods and results of which are presented below. In normal growing rats, a representative compound, [(2-pyridinylamino)methylidene]bisphosphonic acid tetraethylester, decreased spontaneous bone resorption as assessed by urinary tetracycline excretion from chronically prelabeled rats. The said compound was also effective in preventing bone loss in experimental osteoporosis induced by sciatic nerve section in rats. No effect in vitro on resorption of mice calvaria in culture, assayed by calcium release was shown. This may suggest that the compound is metabolized before pharmacological effects can be found. The parent compound did not show either any binding on hydroxyapatite crystals in vitro.

Pharmacokinetics of the compound [(2-pyridinylamino)methylidene]bisphosphonic acid tetraethylester was studied in rats. Minor amounts of an intravenous dose was excreted as a parent compound during 24 hours into urine supporting extensive metabolism as well. About half of the oral dose of the said compound was absorbed in rats.

The following examples illustrate the present invention without limiting the same in any way.

EXAMPLE 1

Synthesis of [(2-Pyridinylamino)methylidene] bisphosphonic acid tetraethylester:

2-Aminopyridine (0.2 moles) was mixed with triethyl orthoformate (0.8 mol) and boron trifluoride etherate and the mixture was heated at 150° C. for 4 h, whereafter the ethanol formed in the reaction was distilled off. Triethylorthoformate was distilled off in vacuum. Diethylphosphite (0.4 mol) was added to the reaction mixture, and the mixture was heated at 150° C. while distilling off the ethanol formed. The mixture was cooled and the raw product was purified chromatographically (eluent dichloromethane-methanol 1:1). Yield 29 g (37%).

The physico-chemical characteristics of this product are as follows:

$^{31}$P-NMR (CDCl$_3$) 15.52 ppm
$^1$H-NMR (CDCl$_3$):

| ppm  | Protons | Multiplicity | Assignation |
|------|---------|--------------|-------------|
| 1.27 | 12 H    | m            | CH$_3$      |
| 4.21 | 8 H     | m            | CH$_2$      |
| 4.78 | 1 H     | d            | NH          |
| 5.57 | 1 H     | dt           | CH          |
| 6.52 | 1 H     | d            | CH (arom)   |
| 6.67 | 1 H     | m            | CH (arom)   |
| 7.44 | 1 H     | m            | CH (arom)   |
| 8.11 | 1 H     | d            | CH (arom)   |

Mass Spectrum (EI Mass):
380 M
334 M-EtOH
243 M-P(O)(O)(OC$_2$H$_5$)$_2$

EXAMPLE 2

Preparation of [[(5-Chloro-2-pyridinyl)amino] methylidene]-bisphosphonic acid tetraethylester 5-Chloro-2-aminopyridine (0.2 moles) was mixed with triethyl orthoformate (0.8 mol) and boron trifluoride etherate and the mixture was heated at 150° C. for 4 h. The formed ethanol was distilled off during the reaction. Triethylorthoformate was distilled off in vacuum. Diethylphosphite (0.4 mol) was added to the reaction mixture, and the mixture was heated at 150° C. while distilling off the ethanol formed. The mixture was cooled and the raw product was purified chromatographically (eluent dichloromethanemethanol, 1:1). Yield 26.5 g (32%). (31-P-NMR 15.20 ppm; CDCl$_3$)

In the same manner may be prepared:
[[(3,5-dichloro-2-pyridinyl)amino]methylidene] bisphosphonic acid tetraethylester (31-P-NMR 14.59 ppm; CDCl$_3$)
[[(3-Chloro-5-trifluoromethyl-pyridinyl)amino] methylidene]-bisphosphonic acid tetraethylester (31-P-NMR 14.15 ppm; CDCl$_3$
[[(5-Hydroxy-2-pyridinyl)amino]methylidene] bisphosphonic acid tetraethylester (Mass Spectrum EI Mass): 396 M, 350 M-EtOH, 259 M-P(O)(OC$_2$H$_5$)$_2$
[[(5-Nitro-2-pyridinyl)amino]methylidene]bisphosphonic acid tetraethylester (31-P-NMR 13.97 ppm; CDCl$_3$)
[[(5-Benzyloxy-2-pyridinyl)amino]methylidene] bisphosphonic acid tetraethylester
[[(5-Methoxy-2-pyridinyl)amino]methylidene] bisphosphonic acid tetraethylester
[[(3,5-Dimethoxy-2-pyridinyl)amino]methylidene] bisphosphonic acid tetraethylester

EXAMPLE 3

Preparation of [[(3-Hydroxy-2-pyridinyl)amino] methylidene]-bisphosphonic acid tetraethylester 2-Amino-3-hydroxypyridine was O-benzylated with benzylchloride in a two phase system and phase transfer catalyst (Bristol et al, Synthesis 1981, 971). 2-Amino-3-benzyloxypyridine (0.1 mol) was dissolved in dichloromethane and the solution was cooled to 0° C. 50 ml Formic acid/aceticanhydride (5:3) was added to the solution, and the mixture was stirred overnight at room temperature. The reaction mixture was concentrated, and the residue was washed with di-isopropylether to give 11.4 g 3-benzyloxypyridinyl-2-formamide. 10 ml Phosphoroustrichloride and 1.5 ml triethylphosphite was heated at 60°–70° C. for 1 hour. 3-Benzyloxypyridinyl-2-formamide (0.01 mol) was added to the solution, and the mixture was stirred for five hours at room temperature. The reaction mixture was concentrated and purified chromatographically (eluent dichloromethane-methanol, 2:1) to get 0.8 g [[(3-benzyloxy-2-pyridinyl)amino]methylidene]bisphosphonic acid tetraethylester. The benzylgroup was hydrogenated to get 0.4 g [[(3-Hydroxy-2-pyridinyl)amino]methylidene]-bisphosphonic acid tetraethylester (Mass Spectrum (EI Mass): 396 M, 350 M-EtOH, 259 M-P(O)(OC$_2$H$_5$)$_2$ In the same manner may be prepared:

[[(6-Benzyloxy-3-pyridinyl)amino]methylidene] bisphosphonic acid tetraethylester

[[(6-Hydroxy-3-pyridinyl)amino]methylidene] bisphosphonic acid tetraethylester

EXAMPLE 4

Preparation of [[(6-Chloro-3-pyridinyl)amino]methylidene]-bisphosphonic acid tetraethylester Diethyl iodomethylphosphonate was prepared according to Cade, J. Chem.Soc. 1959; 2266.

6-Chloro-3-aminopyridine was alkylated with diethyl iodomethylphosphonate, sodium amide as base, with known methods. The obtained 6-chloro-3-pyridinylaminomethylphosphonic acid diethylester (0.5 mol) and N-bromosuccinimid (0.5 mol) in anhydrous carbontetrachloride is irradiated 2 hours with a 200 W lamp. The solid is filtered off, washed with carbontetrachloride and the solution is concentrated in vacuo. The obtained 6-chloro-3-pyridinylamino(bromomethyl)-phosphonic acid diethylester (0.1 mol) is warmed in tetrahydrofuran with triethylphosphite (0.1 mol) in 50° C. for 4 hours. The reaction mixture is concentrated in vacuo. The product is purified chromatographically (eluent dichloromethane: methanol 9:1). Yield 5.1 g.

In the same manner may be prepared:

[[(2-Chloro-3-pyridinyl)amino]methylidene]bisphosphonic acid tetraethylester

[[(6-Methoxy-3-pyridinyl)amino]methylidene] bisphosphonic acid tetraethylester

[(4-Pyridinylamino)methylidene]bisphosphonic acid tetraethylester

[[(6-Amino-2-pyridinyl)amino]methylidene]bisphosphonic acid tetraethylester

[[(3-Nitro-2-pyridinyl)amino]methylidene]bisphosphonic acid tetraethylester

[[(2-Chloro-3-pyridinyl)amino]methylidene]bisphosphonic acid tetraethylester

[[(5-Acyloxy-2-pyridinyl)amino]methylidene] bisphosphonic acid tetraethylester

Effect on spontaneous bone resorption assessed by urinary tetracycline excretion from prelabeled rats Male Sprague-Dawley rats were used. From the first week of life, the rats were injected subcutaneously with a solution containing 10 µCi/ml of (7-$^3$H(N))tetracycline dissolved in physiological saline. The injections were performed twice weekly for 6 weeks. Every animal received a total amount of 20 µCi radiolabeled tetracycline. All animals were given normal diet for growing animals and water ad libitum. One week after the last injection of radiolabeled tetracycline, the rats were weighed and feeding with diet for adult animals was started. At fifth day the rats were randomized into groups and housed in individual metabolic cages. 24-h urine collections were performed for ten days. From the second day [(2-pyridinylamino)methylidene]bisphosphonic acid tetraethylester, compound I, dissolved in physiological saline was injected subcutaneously at different dose levels daily for six days. Control animals received physiological saline. Urine volume was measured and the radioactivity in urine samples was determined by liquid scintillation counting. The data was calculated as the ratio of treated/control at each day for the determination of maximal inhibition of tetracycline excretion.

Excretion of unmetabolized tetracycline into urine reflects its removal from bone during resorptive processes and thus enables the continual monitoring of bone resorption. As shown in Table 1 (compound I) dose-dependently inhibited excreation of radiolabeled tetracycline indicating inhibition of bone resorption.

TABLE 1

Effect on spontaneous bone resorption in rats

| | | Inhibition of tetracycline excretion % | |
|---|---|---|---|
| | | n | Mean (SE) |
| I | 1 mg/kg | 5 | 12.2 (6.4) |
| | 10 mg/kg | 5 | 19.8 (5.9) |
| | 100 mg/kg | 5 | 50.0 (6.1) |
| | 200 mg/kg | 5 | 72.9 (2.6) |

Effect on immobilization induced osteoporosis in rats

Male Sprague-Dawley rats weighing 200±25 g were randomized by weight into groups and anesthetized with Hypnorm/Mebunat and Temgesic. A dorsolateral incision was made on the right or left hip through which the sciatic nerve was exposed, and a 0.5 cm section excised. The muscle and skin were sutured and the animal returned to its cage. The contralateral leg was left intact. The compound I dissolved in physiological saline was administered by subcutaneous injection daily at different dose levels from two days before the surgery until the day of 20 postneurectomy. Control animals received physiological saline. Animals double-labeled with fluorochrome at standardized time points were sacrificed at 21 days postneurectomy and their femora were removed. Femora were embedded in methylmetacrylate, sectioned, and stained. The metphyseal secondary spongiosa and the diaphyseal cortical bone of the femora were subjected to histomorphometric analysis. In control rats, femural total bone area decreased in the immobilized leg. As shown in Table 2 the compound I increased dose-dependently femoral bone area in the immobilized leg. No deleterious effects on mineral apposition rate of cortical bone were shown (data not presented).

TABLE 2

Effect on immobilization induced osteoporosis in rats

| | | Immobilized leg Femur total bone area % | |
|---|---|---|---|
| | | n | Mean (SE) |
| Control | | 20 | 5.3 (0.6) |
| I | 1 mg/kg | 4 | 6.0 (1.3) |
| | 37,5 mg/kg | 5 | 17.3 (2.0) |
| | 75 mg/kg | 5 | 24.5 (2.5) |
| | 200 mg/kg | 7 | 35.5 (1.7) |

Effect on bone in vitro

Newborn mice were labeled by a subcutaneous injection of $^{45}$Ca four days prior to sacrifice. Calvarial bone fragments were microdissected from the parietal bones, preincubated in culture medium with indomethacin, washed and then cultured for three days with and without the compound I. Bone resorption was stimulated by parathyroid hormone (PTH, 10 nM) and an inhibitory effect on this stimulated resorption was measured. As presented in Table 3 no inhibition of resorption in vitro was shown except at very high, unphysiological concentrations. For the determination of the binding of compound I to bone mineral, $^{14}$C-disodium clodronte tetrahydrate and hydroxyapatite crystals were incubated at room temperature in barbituric acid buffer at physiological pH in the absence and presence of the compound I in various concentrations. After two hours incubation, the mixture was centrifuged, and the percent of the total specifically bound radioactivity was measured from the supernatant. No binding of the compound I to hydroxyapatite was found at up to 500 µM concentration (Table 3).

TABLE 3

Effect on bone in vitro

|   |         | Inhibition of PTH-stimulated resorption 100 (PTH − x)/PTH Inhibition % (SE) | Binding to bone mineral |
|---|---------|----|----|
| I | 1 µmol/l | No inhibiton | N.D. |
|   | 5 µmol/l | N.D. | No binding |
|   | 10 µmol/l | No inhibition | N.D. |
|   | 100 µmol/l | No inhibition | No binding |
|   | 200 µmol/l | N.D. | No binding |
|   | 500 µmol/l | N.D. | No binding |
|   | 1000 µmol/l | 12.9 (1.3) | N.D. |

N.D. = Not determined

Pharmacokinetics

Bioavailability was determined from the total amount of compound excreted into urine during 24 hours or from the serum concentration data at different time points after oral administration and intravenous administration. The urine and serum samples were analyzed for the test compound I with high pressure liquid chromatographic methods. Below 10% of the oral dose and 14% of the intravenous dose was excreted as a parent compound during 24 hours (Table 4, bioavailability 58%). Bioavailability of compound I assessed by serum concentration data was 44%.

TABLE 4

Urinary excretion, AUC$_{0 \rightarrow \infty}$, and bioavailability of I after a single intravenous or oral dose*

|      | Excretion 0–24 h | | AUC$_{0 \rightarrow \infty}$ | |
|------|-----------|------|----------|------|
|      | % of dose | F %  | h * µg/ml | F % |
| p.o. | 7.8       | 58   | 60.7     | 44   |
| i.v. | 13.6      |      | 138.7    |      |

Dose 114 mg/kg
F = bioavailability
AUC$_{0 \rightarrow \infty}$ = Area under the blood level-time curve

We claim:

1. Method of treating bone diseases, consisting of osteolytic bone diseases due to malignancy, Paget's disease and primary and secondary osteoporosis, said method comprising administering to a mammal in need of said treatment a pharmaceutically effective amount of a Pyridinyl-aminomethylidenebisphosphonic acid tetraester of the formula

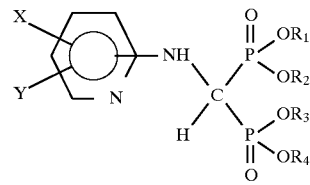

wherein each of $R_1$ to $R_4$ is a straight or branched saturated $C_1$–$C_5$-alkyl group, each of X and Y is independently halogen, hydroxyl, $C_1$–$C_5$-alkoxy, benzyloxy, acyloxy, nitro, a trifluoromethyl group or $NR_5R_6$, wherein $R_5$ and $R_6$ are the same or different and are hydrogen, $C_1$–$C_5$-alkyl or -acyl.

2. The method of claim 1 wherein $C_1$–$C_5$-alkyl of the alkyl group in the alkoxy and the acyl group, is methyl or ethyl, and halogen is chlorine.

3. The method of claim 1 or 2 wherein the groups $R_1$ to $R_4$ are the same.

4. The method of claim 3 wherein the pyridinyl group is 2-pyridinyl.

5. The method of claim 1 wherein the pyridinylaminomethylidenebisphosphonic acid tetraester is one or more of:

[[(3-Hydroxy-2-pyridinyl)amino]methylidene] bisphosphonic acid tetraethylester,

[[(6-Methoxy-3-pyridinyl)amino]methylidene] bisphosphonic acid tetraethylester,

[(4-Pyridinylamino)methylidene]bisphosphonic acid tetraethylester,

[[(5-Chloro-2-pyridinyl)amino]methylidene]bisphosphonic acid tetraethylester,

[[(5-Methoxy-2-pyridinyl)amino]methylidene] bisphosphonic acid tetraethylester,

[[(6-Amino-2-pyridinyl)amino]methylidene]bisphosphonic acid tetraethylester,

[[(3-Nitro-2-pyridinyl)amino]methylidene]bisphosphonic acid tetraethylester,

[[(3,5-Dichloro-2-pyridinyl)amino]methylidene] bisphosphonic acid tetraethylester,

[[(6-Hydroxy-3-pyridinyl)amino]methylidene] bisphosphonic acid tetraethylester,

[[(5-Hydroxy-2-pyridinyl)amino]methylidene] bisphosphonic acid tetraethylester,

[[(3-Chloro-5-trifluoromethyl-pyridinyl)amino] methylidene]-bisphosphonic acid tetraethylester,

[[(2-Chloro-3-pyridinyl)aminio]methylidene]bisphosphonic acid tetraethylester,

[[(6-Chloro-3-pyridinyl)amino]methylidene]bisphosphonic acid tetraethylester,

[[(3-Benzyloxy-2-pyridinyl)amino]methylidene] bisphosphonic acid tetraethylester,

[[(5-Nitro-2-pyridinyl)amino]methylidene]bisphosphonic acid tetraethylester, or

[[(5-Benzyloxy-2-pyridinyl)amino]methylidene] bisphosphonic acid tetraethylester.

6. The method of claim 1 wherein the pyridinylaminomethylidenebisphosphonic acid tetraester is administered as an admixture with a pharmaceutically acceptable carrier.

* * * * *